United States Patent [19]
Birkle et al.

[11] Patent Number: 5,552,027
[45] Date of Patent: Sep. 3, 1996

[54] WORKING ELECTRODE FOR ELECTROCHEMICAL ENZYMATIC SENSOR SYSTEMS

[75] Inventors: Siegfried Birkle, Hoechstadt; Johann Kammermaier, deceased, late of Unterhaching, by Rosemarie Kammermaier, heir; Rolf Schulte, Erlangen, all of Germany

[73] Assignee: Siemens Aktiengesellschaft, München, Germany

[21] Appl. No.: 503,563

[22] Filed: Jul. 18, 1995

Related U.S. Application Data

[63] Continuation of Ser. No. 287,025, Aug. 18, 1994, abandoned.

[30] Foreign Application Priority Data

Sep. 22, 1993 [DE] Germany ............... 43 32 251.4

[51] Int. Cl.⁶ ............... G01N 27/26; C25B 11/00
[52] U.S. Cl. .............. 204/290 F; 204/403; 204/400; 204/192.1; 204/192.12; 427/450; 427/528; 427/569; 427/249; 427/255.1; 427/327; 427/330; 437/101; 437/103; 437/225; 437/228; 148/240; 148/281; 148/DIG. 1
[58] Field of Search .................... 437/101, 102, 437/103, 225, 228–233; 427/450, 528, 569, 249, 255, 255.1, 255.2, 327, 330, 419.1, 419.2; 148/DIG. 1, 240, 281; 204/290 F, 403, 400, 192.1, 192.12, 192.16

[56] References Cited

U.S. PATENT DOCUMENTS

| | | | |
|---|---|---|---|
| 5,039,358 | 8/1991 | Birkle et al. | 437/101 |
| 5,055,421 | 10/1991 | Birkle et al. | 437/101 |
| 5,162,875 | 11/1992 | Birkle et al. | 257/636 |

FOREIGN PATENT DOCUMENTS 0470290  2/1992  European Pat. Off. .

OTHER PUBLICATIONS

Koeberle, H. et al., "A Microstructural Investigation of Au-a-C:H Films", *Surface and Coatings Technology*, vol. 39/40 (1989), pp. 275–284. No month available.

Harnack, J. et al., "Target Effects During the Deposition of Ti-a-C:H Films", *Surface and Coatings Technology*, vol. 39/40, pp. 285–292. No month/yr. available.

IDR—Industrie Diamanten Rundschau, Bd. 18 (1984), p. 249–253. No month available.

*Primary Examiner*—Bruce F. Bell
*Attorney, Agent, or Firm*—Kenyon & Kenyon

[57] ABSTRACT

A working electrode or an electrochemical-enzymatic sensor system has a metallic base body which is provided with a thin layer of amorphous hydrogenated carbon (a-C:H).

18 Claims, No Drawings

WORKING ELECTRODE FOR ELECTROCHEMICAL ENZYMATIC SENSOR SYSTEMS

This application is a continuation of application Ser. No. 08/287,025 filed Aug. 8, 1994 now abandoned.

BACKGROUND OF THE INVENTION

1. Field of the Invention

The present invention relates to a working electrode for electrochemical-enzymatic sensor systems and to a method of producing such a working electrode.

2. Description of Related Art

For the medical detection of metabolic processes in body fluids, for instance, glucose reaction, sensor systems are used in which changes in electrochemical potential which are produced by enzymatic reactions serve as characteristic value. The following requirements are made on the working electrodes of such sensor systems:

electrical conductivity $> 10^{-2}\ \Omega^{-1}\ cm^{-1}$ variability of shape for special electrode geometries chemically inert character, particularly with regard to the electrochemically produced reaction products compatibility of the electrode material with the human body smooth surfaces without roughnesses or grain boundaries for avoiding the danger of a thrombosis upon the implantation.

From EP-OS 0 470 290 an electrochemical-enzymatic sensor for the determining of substances in body fluids, particularly glucose, is known. This sensor has the following characteristics:

a sensor electrode of electrocatalytically inactive carbon a counter electrode a reference electrode an enzyme-containing layer present in front of the sensor electrode, and a membrane of biocompatible, hydrophilic oxygen-pervious material which covers the enzyme layer off from the body fluid and holds the enzyme back.

In this sensor, the material for the sensor electrode, which is also known as working electrode or measurement electrode, consists of vitreous carbon, pyrographite, sputtered carbon, sputtered graphite or amorphous hydrogenated carbon. Vitreous carbon is preferred, namely in the form of a smooth vitreous-carbon electrode.

Vitreous carbon is generally produced by pyrolysis of polyfurfuryl alcohol. This material, as carbon modification—is sufficiently inert chemically and, on basis of its amorphous structure, it has a smooth surface. It is suitable for implantation. Vitreous carbon also satisfies the requirements with regard to electric conductivity. However, one disadvantage is that vitreous carbon is difficult to contact. Furthermore, vitreous carbon requires costly processing since cracks can easily occur in thin layers upon the high-temperature pyrolysis involved in its production.

SUMMARY OF THE INVENTION

The object of the present invention is to provide a working electrode for electrochemical-enzymatic sensor systems which fully satisfies the requirements made on such an electrode.

This is achieved, in accordance with the invention, by providing a working electrode having a metallic base body which is provided with a thin layer of amorphous hydrogenated carbon (a-C:H).

DETAILED DESCRIPTION OF THE INVENTION

Amorphous hydrogenated carbon is a carbon modification having diamond-like mechanical and chemical properties, which forms pinhole-free, smooth surfaces (see, for instance: "IDR-Industrie Diamanten Rundschau" Vol. 18 (1984), pages 249 to 253). Surfaces coated with a-C:H are tissue compatible in the same way as vitreous carbon and are inert with respect to body fluids, such as blood. One basic difference from diamond is that the electrical resistance can be controlled intrinsically within a wide range by the conditions of deposition, conductivities which are comparable even to graphite are obtainable (up to $10^{-1}\ \Omega^{-1}\ cm^{-1}$). The amorphous structure of a-C:H results from the presence of $sp^3$ and $sp^2$ bonds of the C atoms and it is stabilized by chemically bound H atoms (maximum proportion: about 60 vol. %) at temperatures up to about 500° C.

The a-C:H layer preferably has a thickness of < 5 μm. The metallic base body consists preferably of titanium; in addition, however, metals such as zirconium, molybdenum and tungsten are also suitable, as well as highly doped, electrically conductive silicon.

For the production of the working electrode of the invention and for the deposition of the thin layer of a-C:H on the metallic base body, a low-pressure plasma deposition with high frequency excitation is used; the operating frequency is for instance 13.56 MHz. Hydrocarbons, particularly $CH_4$, $C_2H_4$ and $C_6H_6$, are used as process gas, preferably at an operating pressure of between 1 and 100 Pa. The HF power density in the plasma is preferably between 0.1 and 10 $W.cm^{-3}$. With unequal electrode surfaces (ratio between about 0.1 and 0.5) a DC self-bias voltage of up to 1100V is established, the smaller electrode being the cathode. Due to this DC self-bias voltage, the a-C:H formation takes place predominantly as an ion deposition process with a very high energy of the $C_xH_y$ particles impinging on the substrate. In this way, there is obtained both a high proportion of diamond-like $sp^3$ bonds of the C atoms in the a-C:H layer and also—due to a carbide formation in the boundary layer—a high adherence strength of the a-C:H layer to the metallic base body. In contrast to this, this is not true upon the CVD deposition of pyrocarbon or upon the pyrolytic deposition of vitreous carbon.

The shape of the electrodes (in the deposition reactor) is adapted to the shape of the metallic base body to be coated. Thus, for instance, in the case of flat substrate surfaces, electrodes of different sizes having flat, parallel surfaces are used, while in the case of curved base bodies correspondingly shaped, for instance spherically shaped, pairs of electrodes are employed in order to obtain a sufficient DC self-bias effect.

One advantageous embodiment of the invention is in including metal clusters of, for instance, gold or titanium in the a-C:H layer during the plasma deposition from a target present in the deposition reactor in order to improve the electric conductivity (see in this connection also; "Surface and Coatings Technology," Vol. 39/40 (1989), pages 275 to 284 and 285 to 292). In this case, the a-C:H deposition is carried out under changed conditions, i.e. the substrate is positioned on the anode. The cathode bears the target from which the metal atoms are split off by impinging $C_xH_y$ ions or Ar ions.

The invention will be further explained on the basis of embodiments.

EXAMPLE 1

An a-C:H layer of a thickness of about 1.8 µm is deposited on a flat sheet of titanium of a thickness of 0.25 mm which has been cleaned with a solvent and subjected to a preliminary plasma treatment with argon in accordance with the conditions described below. Methane is used as process gas; the operating pressure is 20 Pa. With an electrode-surface ratio of about 0.16 between the electrode bearing the substrate and the cup-shaped counter electrode—with an operating frequency of 13.56 MHz and an HF power density of 0.3 W.cm$^{-3}$ —a DC self-bias voltage of about 850V is established in the plasma, the smaller electrode (surface: 44.2 cm$^2$) being the cathode. The a-C:H layer obtained has a specific electric resistivity of about $10^4$ Ω.cm. The titanium electrode which has been coated in this manner exhibits a very small double-layer capacitance of 4.4 µF.cm$^{-2}$ in electrochemical measurements, which indicates a very smooth and dense a-C:H coating.

EXAMPLE 2

In the same way as in Example 1, with an operating pressure of 3.5 Pa, an HF power density in the plasma of 6.5 W.cm$^{-3}$, a DC self-bias voltage of about 1100V, and using flat electrodes with a surface ratio of about 0.27, other conditions being the same, a-C:H layers of a thickness of 0.4 µm having an electrical resistance of only 7 Ω.cm are obtained on base bodies of titanium.

What is claimed is:

1. A working electrode for an electrochemical-enzymatic sensor system, comprising a base body of titanium, zirconium, molybdenum, tungsten or electrically conductive silicon, the base body having a thin layer consisting essentially of amorphous hydrogenated carbon (a-C:H).

2. The working electrode according to claim 1 wherein the a-C:H layer has a thickness of < 5 µm.

3. The working electrode according to claim 2 wherein the metallic base body consists of titanium.

4. The working electrode according to claim 3 wherein the a-C:H layer contains metal clusters.

5. The working electrode according to claim 2 wherein the a-C:H layer contains metal clusters.

6. The working electrode according to claim 1 wherein the metallic base body consists of titanium.

7. The working electrode according to claim 6 wherein the a-C:H layer contains metal clusters.

8. The working electrode according to claim 1 wherein the a-C:H layer contains metal clusters.

9. The working electrode according to claim 8 wherein the metal clusters are clusters of gold or titanium.

10. A method of producing a working electrode for an electrochemical-enzymatic sensor system, comprising the step of depositing a thin layer consisting essentially of amorphous hydrogenated carbon (a-C:H) on a base body of titanium, zirconium, molybdenum, tungsten or electrically conductive silicon, by low-pressure, high-frequency plasma deposition of a gaseous hydrocarbon.

11. The method according to claim 10 wherein the plasma deposition takes place at a pressure of 1 to 100 Pa.

12. The method according to claim 11 wherein the high-frequency power density in the plasma is 0.1 to 10 W.cm$^{-3}$.

13. The method according to claim 11 wherein the plasma deposition takes place with a DC self-bias voltage of up to 1100V.

14. The method according to claim 10 wherein the high-frequency power density in the plasma is 0.1 to 10 W.cm$^{-3}$.

15. The method according to claim 14 wherein the plasma deposition takes place with a DC self-bias voltage of up to 1100V.

16. The method according to claim 10 wherein the plasma deposition takes place with a DC self-bias voltage of up to 1100V.

17. The method according to claim 10 wherein the hydrocarbon used is methane.

18. The method according to claim 10 wherein metal clusters are incorporated in the a-C:H layer.

* * * * *